United States Patent [19]

Ganne

[11] Patent Number: 5,801,157
[45] Date of Patent: Sep. 1, 1998

[54] COMPOSITION COMPRISING A RECOMBINANT PLASMID AND ITS USES AS VACCINE AND MEDICAMENT

[75] Inventor: Vincent Ganne, La Varenne Saint Hilaire, France

[73] Assignee: Societe D'Exploitation de Produits Pour L'Industrie Chimique S.E.P.P.I.C., Paris, France

[21] Appl. No.: 704,572

[22] PCT Filed: Mar. 21, 1995

[86] PCT No.: PCT/FR95/00345

§ 371 Date: Sep. 9, 1996

§ 102(e) Date: Sep. 9, 1996

[87] PCT Pub. No.: WO95/25542

PCT Pub. Date: Sep. 28, 1995

[30] Foreign Application Priority Data

Mar. 22, 1994 [FR] France .................................. 94/03361

[51] Int. Cl.$^6$ .......................... A61K 45/00; A61K 47/44; A61K 48/00; C07H 21/02
[52] U.S. Cl. .......................... 514/44; 424/278.1; 536/23.1
[58] Field of Search .......................... 514/44; 424/278.1; 110/115; 935/53, 55, 60, 65; 536/23.1

[56] References Cited

FOREIGN PATENT DOCUMENTS

WO 91/00106  1/1991  WIPO .
WO 94/16681  8/1994  WIPO .

OTHER PUBLICATIONS

Liu, F. et al (1996). Pharmaceutical Research 13, 1642–46.
Orkin, S. et al (1995). Report and Recommendations of the Panel to Assess The NIH Investment in Research in Gene Therapy.
Mulligan, R. (1993). Science 260, 926–930.
Ganne, V. (1994). Vaccine 12, 1190–6.
Haddada, H. et al. (1993). Biochemical and Biophysical Research Communications 195, 1174–83.
Roitt, I. (1994). Essential Immunology, Blackwell Scientific Publications, pp. 288–289.
by Lin, Hua et al., "Expression of Recombinant Genes in Myocardium In Vivo After Direct Injection of DNA", *Circulation*, vol. 82, No. 6, Dec. 1990, pp. 2217–2221.
by Cox, Graham J.M. et al., "Bovine Herpesvirus 1: Immune Responses in Mice and Cattle Injected with Plasmid DNA", *Journal of Virology*, vol. 67, No. 9, Sep. 1993, pp. 5664–5667.

*Primary Examiner*—Brian R. Stanton
*Attorney, Agent, or Firm*—Young & Thompson

[57] ABSTRACT

A composition containing a recombinant plasmid which includes an exogenous nucleotide sequence capable of expressing a compound including an amino acid sequence in a host organism. The composition includes an emulsion comprising at least one aqueous phase and at least one oily phase, the recombinant plasmid being contained in at least one of phases. A vaccine and a curative drug including the composition are also disclosed.

7 Claims, 1 Drawing Sheet

COMPOSITION COMPRISING A RECOMBINANT PLASMID AND ITS USES AS VACCINE AND MEDICAMENT

BACKGROUND OF THE INVENTION

1. Field of the Invention

The present invention relates to a new composition comprising a recombinant plasmid, as well as to vaccines or curative medicaments comprising such a composition.

2. Description of the Related Art

Vaccination with live viruses or microorganisms has numerous well-known advantages compared to vaccination with non-live vaccines consisting of killed microorganisms or of isolated proteins or peptides.

Live vaccines consist of a live microorganism or a live virus. These latter are generally attenuated so as to decrease the pathogenic risks. However, this risk is never completely eliminated inasmuch as, in particular, a reversion of the microorganism or virus to a virulent form may occur.

Moreover, the mutations or deletions employed in order to bring about an attenuation of the virulence of the strains sometimes cause a decrease in the immune response, necessitating the injection of large doses of vaccines. Recently, new vaccines whose preparation has been made possible by the advances in genetic engineering have been developed. Among these new vaccines, there may be mentioned those consisting of a recombinant plasmid formed from a nucleotide sequence into which is inserted an exogenous nucleotide sequence originating from a microorganism or from a pathogenic virus. The purpose of the latter nucleotide sequence is to permit the expression of a compound comprising an amino acid sequence, the purpose of this compound itself being to trigger an immune reaction in a host body.

The first injection of such a plasmid, as well as its expression in a muscle, was performed and demonstrated in 1990 by Lin et al. (Circulation 82:2217–2221). The object of this experiment was to demonstrate that a recombinant plasmid injected into a living organism was capable of expressing the exogenous sequence in the tissues into which had been injected. It was demonstrated in this way that the administration of a recombinant plasmid to a living organism could be used in gene therapy. This therapeutic method is well known and consists, in particular, in administering to a host body genetically modified cells or, as demonstrated by Lin et al., recombinant plasmids capable of expressing compounds synthesized by living organisms, such as peptides, proteins or glycoproteins. The purpose of the in vivo synthesis of these compounds can be either to compensate for a deficiency of a genetic nature in the host body to which the genetically modified cells of the recombinant plasmids have been administered, or to have a curative action against a disease, such as a cancer, triggered in this same host body.

As an example, such a curative action may consist of a synthesis, by recombinant cells or recombinant plasmids, of cytokines such as interleukins, in particular interleukin-2. These cytokines enable an immune reaction directed towards the selective elimination of cancer cells to be triggered or enhanced.

Subsequently, it was shown that recombinant plasmids carrying a specific gene, coding for the glycoprotein of bovine herpesvirus I (BHV-1), were capable of inducing an immune response, consisting of the synthesis of antibody, in different animal species, namely mice and cattle (Cox et al., J. Virol. September 1993, 67, 9, 5664, 5667). However, this study also shows clearly a heterogeneity of the immune responses obtained. In other words, all other conditions being equal, the immune response is highly variable for each animal tested and each injection performed. It emerges from this that a few animals display a low level of antibodies, though sometimes sufficient to induce some degree of protection, whereas most of the other animals do not display an antibody level of this kind. In the latter case, no protection is induced.

SUMMARY OF THE INVENTION

The present invention thus consists of a composition comprising a recombinant plasmid capable of expressing, in a host body to which said recombinant plasmid has been administered, a larger amount of compounds of the peptide, protein or glycoprotein type.

Another subject of the invention consists of a composition containing a recombinant plasmid at a concentration lower than that in traditional compositions, with a view to an expression of compounds of the peptide, protein or glycoprotein type in an unchanged or even a larger amount.

Another subject of the invention consists of a vaccine comprising a composition containing a recombinant plasmid enabling a more homogeneous immune response and an enhanced protection against a virus or a pathogenic microorganism to be obtained.

Yet another subject of the invention consists of a curative medicament comprising a composition containing a recombinant plasmid capable of expressing increased amounts of molecules of the peptide, protein or glycoprotein type, and of being employed with a reduced concentration of recombinant plasmids.

Thus the invention consists of a composition containing a recombinant plasmid comprising an exogenous nucleotide sequence capable of expressing a compound comprising an amino acid sequence in a host body, characterized in that said composition comprises an emulsion containing at least one aqueous phase and at least one oil phase, said recombinant plasmid being contained in at least one of said phases.

BRIEF DESCRIPTION OF THE DRAWING

The FIGURE shows the results of a challenge resistance test performed on mice to which either a recombinant plasmid carrying the GP50 gene of the Aujeszky virus or various controls was/were administered.

DESCRIPTION OF THE PREFERRED EMBODIMENT

Figure 1:
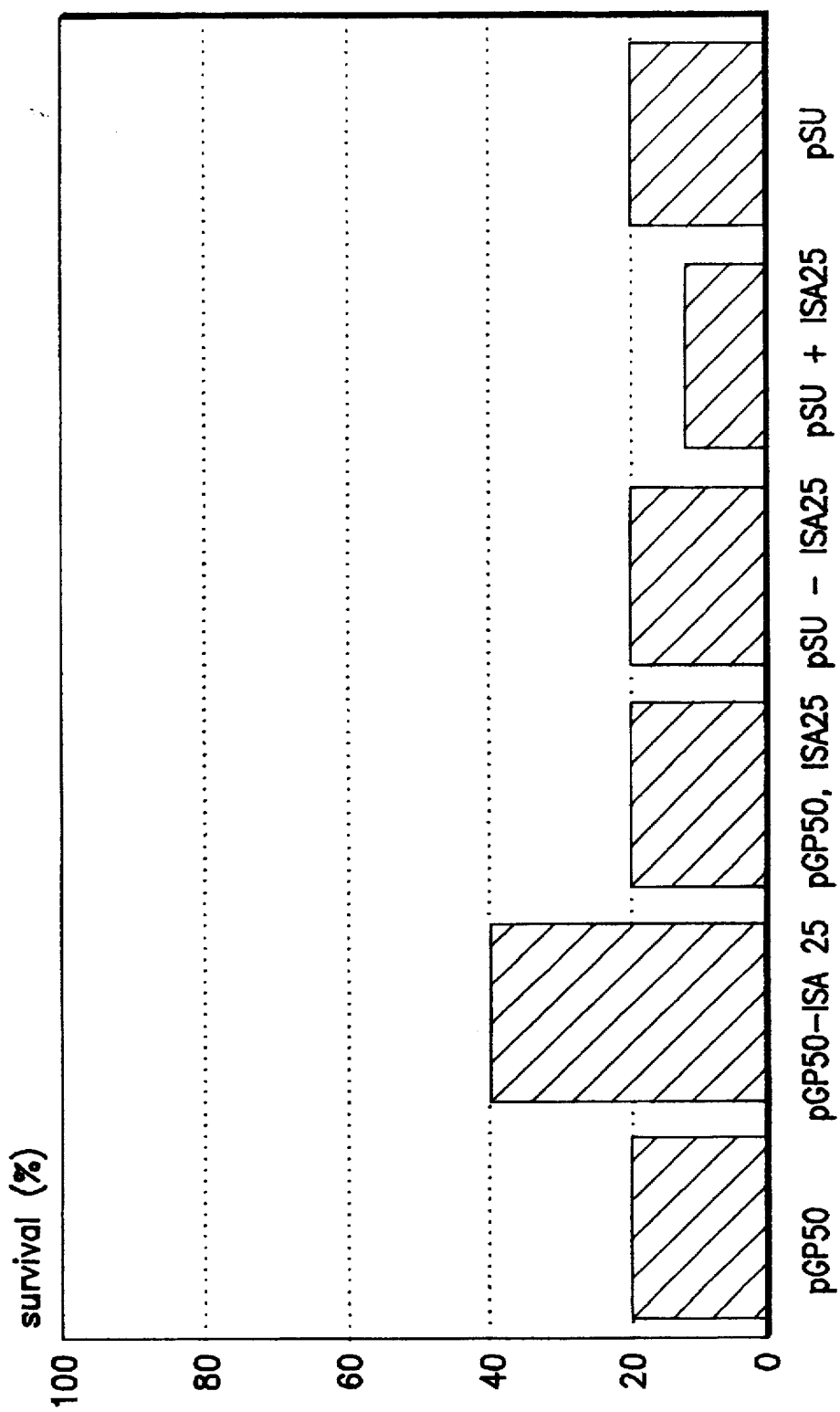

A recombinant plasmid according to the invention may be prepared according to standard methods, for example the method described in the paper by Cox et al., J. Virol., September 1993, 67, 9, 5664–5667, mentioned above, or in the paper by M. Eloit et al., J. of General Virol (1990), 71, 2425–2431 (especially FIG. 1). The teaching of the latter paper is incorporated herein for reference. Naturally, the exogenous nucleotide sequence varies in accordance with the compound to be expressed.

The compound capable of being expressed by the recombinant plasmid when it has been administered to the host body can be a peptide, a protein or a glycoprotein.

This compound can consist, in particular, of an antigen capable of triggering in said host body an immune reaction with respect to a pathogenic virus or to a pathogenic microorganism. This immune reaction may be of the humoral or cellular type, and may consist, in particular, of a synthesis of antibody enabling a protection with respect to such a virus or such a microorganism to be conferred on the host body. By way of such pathogenic viruses, the Aujesky virus, an HIV virus such as HIV-I or HIV-II, an FIV virus or a flu virus of the influenzae type may be mentioned in particular. In context of the present invention, microorganism is understood to mean a bacterium, a yeast, a fungus, a mycoplasma or a unicellular parasite. By way of pathogenic bacteria, furunculoses [sic], *Escherichia coli* or bacteria of the genera Pastorella, Salmonella or Yersinia may be mentioned in particular. By way of pathogenic yeasts, those of the genus Candida, such as *Candida albicans*, may be mentioned. By way of unicellular parasites, *Plasmodium falciparum* or parasites of the genus Leishmania may be mentioned.

Usually, the exogenous nucleotide sequence originates from such a pathogenic virus or microorganism.

Alternatively, the recombinant plasmid administered to the recipient host can comprise a nucleotide sequence capable of expressing a compound comprising an amino acid sequence, such as a peptide, a protein or a glycoprotein, having a curative action with respect to a disease, especially a noninfectious disease possibly of a functional nature which has been triggered in the host body. In this case, the recombinant plasmid permits a therapeutic treatment of the gene therapy type as defined above. Thus, the function of said compound may be to compensate for a deficiency of a genetic nature in the host body, for the purpose of treating a genetic disease such as cystic fibrosis or myopathy. Said compound may also have a curative action with respect to a functional disease which has become manifest in the host body; for example, it may have a curative action with respect to cancer cells. This curative action may consist of the synthesis of cytokines, for instance interleukins such as interleukin-2.

The host body in which said recombinant plasmid must be capable of expressing a compound comprising an amino acid sequence may be an animal, or even a tissue of an animal, such as an insect or a vertebrate animal, especially a mammal, a fish or a bird. Such a mammal may be man, a canine, a bovine, a pig, a rabbit, an ovine or a feline. By way of a bird, gallinaceans such as chickens may be mentioned.

A composition according to the invention can contain an oil-in-water (O/W), water-in-oil (W/O) or water-in-oil-in-water (W/O/W) type emulsion. An especially preferred type of emulsion in the context of the invention consists of an O/W emulsion. An emulsion according to the invention may be prepared according to traditional methods of preparation of an emulsion, in particular according to the processes described in Patent Applications EP-A-489,181 and EP-A-481,982. Thus, the oil constituting the oil phase may be emulsified while stirring it with the aqueous phase consisting of an aqueous solution or suspension containing the recombinant plasmid. Alternatively, the composition of the invention may be prepared by emulsifying an oil comprising the recombinant plasmid, for example in lyophilized form, with an aqueous phase.

An emulsion according to the invention can contain, by weight, from 5 to 95% of oil phase for 95 to 5% of aqueous phase, and preferably from 25 to 75% of oil phase for 75 to 25% of aqueous phase. The emulsion must be stable, preferably for at least 12 months when it is stored at 4° C.

The oil constituting the oil phase can be a mineral oil, a nonmineral oil or a mixture of a mineral oil and a nonmineral oil. Said mineral oils may be natural or synthetic. Said nonmineral oils may be of vegetable, animal or synthetic origin. All these oils lack toxic effects with respect to the host body to which the composition of the invention is administered. They are preferably liquid at the storage temperature (approximately +4° C.), or at least to make it possible [sic] to give liquid emulsions at this temperature. An advantageous mineral oil according to the invention can consist of an oil comprising a linear carbon chain having a number of carbon atoms which is preferably greater than 16, and free from aromatic compounds. Such oils can be, for example, those marketed under the name "MARCOL 52" (produced by Esso France) or "DRAKEOL 6VR" (produced by Penreco USA), which are both commercial mineral oils having a linear hydrocarbon chain, free of aromatic compounds.

By way of synthetic organic oils, polyisobutenes or polyisopropenes may be mentioned. Among vegetable oils, oleic acid-rich unsaturated oils which are biodegradable may be mentioned, for example groundnut, olive, sesame, soybean or wheat germ oils.

The animal oils can consist, in particular, of squalene, squalane or spermaceti oil.

Besides the oil phase and the aqueous phase, the composition according to the invention, in particular when it is used as vaccine, may contain an immune stimulating agent such as avridine.

Moreover, the composition according to the invention may also advantageously contain a surfactant. The latter displays a lipophilic or hydrophilic character characterized by an HLB (hydrophilic-lipophilic balance) value of between 1 and 19.

A preferred surfactant in the context of the present invention can consist of an ester obtained by condensing a fatty acid, advantageously a fatty acid which is liquid at 20° C., with a sugar or glycerol. Said sugar can consist of glucose, sucrose or, preferably, mannitol. By way of an especially preferred mannitol ester, there may be mentioned mannitol oleates obtained by anhydridizing the polyhydroxylated carbon chain of mannitol which is cyclized at positions 1–4 or 2–6.

Derivatives of these esters may also be employed. These derivatives display a hydrophilicity which is modified, in particular, by grafting of hydrophilic functions such as alcohol, polyol, ethylene oxide, propylene oxide, carboxylic acid, amine or amide. A surfactant according to the invention is preferably pharmaceutically acceptable for use as an injectable preparation; it must, in particular, lack heavy metals and possess very low acid or peroxide values. It is also desirable for it to satisfy the specifications of a safety test such as, for example, the one described by S. S. Berlin, Annales of Allergy, 1962, 20, 473. Preferably, the surfactant is combined with the oil before formation of the emulsion.

Oils combined with a surfactant which are most especially suitable in the context of the present invention are those marketed by the company SEPPIC under the brand name "MONTANIDE" (mixture of oil and surfactant). The properties of these oils appear in Table 1 below.

TABLE 1

| No. | Trade name | Oil | Emulsion type | Aqueous phase/ emulsion (% by weight) | Viscosity (mPa · s) | Conductivity at 25° C. (μS · cm$^{-1}$) |
|---|---|---|---|---|---|---|
| 1 | MONTANIDE ISA 25 | Mineral | O/W | 75% | 20 | 5000 |
| 2 | MONTANIDE ISA 25A | Mineral + avridine* | O/W | 75% | 20 | 5000 |
| 3 | MONTANIDE ISA 28 | Mineral + nonmineral | O/W | 75% | 25 | 1000 |
| 4 | MONTANIDE ISA 206 | Mineral | W/O/W | 50% | 50 | 1000 |
| 5 | MONTANIDE ISA 50 | Mineral | W/O | 50% | 200 | 1 |
| 6 | MONTANIDE ISA 708 | Nonmineral | W/O | 30% | 70 | 1 |

*Avridine = N,N-Dioctadecyl-N-bis(2-hydroxy-ethyl)propanediamine.

A composition according to the invention possesses a viscosity of less than 300 mPa.s, and advantageously less than 200 mPa.s, measured at 25° C. by means of a Brookfield type rotational viscometer. The "oily" or "aqueous" character of the continuous phase of the emulsion is characterized by the conductivity measured in microsiemens per cm (μS.cm$^{-1}$) at 25° C. Values below 20 μS.cm$^{-1}$ indicate the presence of a continuous oil phase.

A composition according to the invention comprises an amount of recombinant plasmid which is variable in accordance, mainly, with the host body and the nature of the compound expressed by said plasmid.

Usually, a composition according to the invention can comprise from 0.01 to 100 g/l of said recombinant plasmid.

According to another aspect, the invention also relates to a vaccine comprising a composition as defined above. The purpose of such a vaccine is to provoke an immune reaction against a virus or a pathogenic microorganism such as the ones mentioned above.

According to yet another aspect, the invention relates to a curative medicament comprising a composition as defined below. The purpose of such a medicament is to treat a disease, in particular a functional disease of the host body to which it is administered.

These vaccines and curative medicaments comprising said composition are generally in an injectable form. The host body to which they can be administered are the animals or even animal tissues mentioned above. Man, dogs, cats, poultry, oxen, sheep, pigs and horses will be mentioned here more especially.

The dose of recombinant plasmid contained in said composition to be administered depends on the nature of the host body. This dose of recombinant plasmid can thus vary very widely between 1 μg and 500 mg/kg host body weight.

As an example, it is possible to administer a dose of recombinant plasmid of 500 mg/kg to a mouse weighing 20 g, of 1 μg/kg to an ox weighing 500 kg and a dose of 100 μg to 100 mg/kg, and preferably 1 mg to 30 mg/kg, in an adult human.

A composition according to the invention may be used more especially to prepare a vaccine intended to produce an immune reaction in a host body, for prevention against an HIV virus (in particular in man), an Aujeszky virus (in particular in pigs) or an FIV virus (in particular in cats).

A composition according to the invention may also be used to prepare a medicament intended to treat a cancer.

The purpose of the examples which follow is to illustrate the present invention.

All these examples employ a recombinant plasmid carrying the gp50 gene of the Aujeszky virus. This was obtained according to the method described in the paper by M. Eloit et al., J. of General Virol (1990), 71, 2425–2431 (especially FIG. 1) mentioned above.

In these examples, the following terms mean:

pGP50–ISA 25 (according to the invention): a vaccine containing said recombinant plasmid carrying the GP50 gene of the Aujeszky virus in an emulsion containing MONTANIDE ISA 25 as oil phase (see Table 1);

pGP50+ISA 25 (not according to the invention): a vaccine injected in two stages: in a first stage, an aqueous suspension containing said recombinant plasmid carrying the GP50 gene of the Aujeszky virus is injected, and in a second stage, an emulsion (not containing any plasmid) containing MONTANIDE ISA is injected;

pGP50 (not according to the invention): a vaccine consisting only of an aqueous phase comprising the recombinant plasmid;

pSU–ISA 25 (control): a vaccine similar to pGP50–ISA 25, but comprising a control plasmid expressing an exogenous protein pSU, different from pGP50;

pSU+ISA 25 (control): a vaccine similar to pGP50–ISA 25, but comprising a control plasmid expressing pSU instead of pGP50;

pSU: a vaccine similar to pGP50, but comprising a control plasmid expressing pSU instead of pGP50.

EXAMPLE 1

Mice numbered 1 to 6 are injected with different vaccines.

At regular intervals, the antibodies produced by these vaccines are assayed. For this purpose, the serum is drawn from the mice and the anti-GP50 antibodies are assayed by an ELISA technique described by M. Eloit et al. in Veterinary Record, 1989, 124, 91–94. The results appear in Tables 2 to 5 below. They are expressed in terms of the last dilution necessary for obtaining an optical density above the background.

The results obtained show that a vaccine according to the invention makes it possible to obtain an antibody level markedly higher than that obtained with the comparative vaccines or the controls, as well as a greater homogeneity of the immune response. This homogeneity manifests itself in the obtaining of a high level of antibody, enabling an effective protection to be induced in a larger number of animals.

TABLE 2

Titration of anti-GP50 antibodies by ELISA assay 2 weeks after vaccination:

| Vaccine | mouse 1 | mouse 2 | mouse 3 | mouse 4 | mouse 5 | mouse 6 |
|---|---|---|---|---|---|---|
| pGP50 − ISA 25 | 32 | 1024 | 32 | 1024 | — | — |
| pGP50 + ISA 25 | 16 | 16 | 32 | 16 | — | — |
| PGP50 | 16 | 8 | 8 | 16 | 256 | 16 |
| pSU − ISA 25 | <8 | <8 | <8 | <8 | — | — |
| pSU + ISA 25 | <8 | <8 | <8 | <8 | — | — |
| pSU | <8 | <8 | <8 | <8 | — | — |

TABLE 3

Titration of anti-GP50 antibodies by ELISA assay 4 weeks after vaccination:

| Vaccine | mouse 1 | mouse 2 | mouse 3 | mouse 4 | mouse 5 | mouse 6 |
|---|---|---|---|---|---|---|
| pGP50 − ISA 25 | 32 | 384 | 32 | 1024 | — | — |
| pGP50 + ISA 25 | 16 | 8 | 8 | 8 | — | — |
| pGP50 | 16 | 8 | 8 | 16 | 128 | 8 |
| pSU − ISA 25 | <8 | <8 | <8 | <8 | — | — |
| pSU + ISA 25 | <8 | <8 | <8 | <8 | — | — |
| pSU | <8 | <8 | <8 | <8 | — | — |

TABLE 4

Titration of anti-GP50 antibodies by ELISA assay 6 weeks after vaccination:

| Vaccine | mouse 1 | mouse 2 | mouse 3 | mouse 4 | mouse 5 | mouse 6 |
|---|---|---|---|---|---|---|
| pGP50 − ISA 25 | 1536 | 2048 | — | 2048 | — | — |
| pGP50 + ISA 25 | 128 | 128 | 128 | 48 | — | — |
| pGP50 | 384 | 64 | 256 | 512 | 128 | 128 |
| pSU − ISA 25 | <8 | <8 | <8 | <8 | — | — |
| pSU + ISA 25 | <8 | <8 | <8 | <8 | — | — |
| pSU | <8 | <8 | <8 | <8 | — | — |

TABLE 5

Titration of anti-GP50 antibodies by ELISA assay 3 months after vaccination:

| Vaccine | mouse 1 | mouse 2 | mouse 3 | mouse 4 | mouse 5 | mouse 6 |
|---|---|---|---|---|---|---|
| pGP50 − ISA 25 | 2048 | 1280 | — | 768 | — | — |
| pGP50 + ISA 25 | 256 | 256 | 256 | 256 | — | — |
| pGP50 | 384 | 128 | 256 | 256 | 192 | 256 |
| pSU − ISA 25 | <8 | <8 | <8 | <8 | — | — |
| pSU + ISA 25 | <8 | <8 | <8 | <8 | — | — |
| pSU | <8 | <8 | <8 | <8 | — | — |

EXAMPLE 2

6 groups of 6 mice each are vaccinated with a different vaccine:

pGP50,
pGP50–ISA 25,
pGP50+ISA 25,
pSU–ISA 25,
PSU+ISA 25, and
pSU.

Six weeks after injection of the vaccine, each mouse is injected with an aqueous suspension containing a virulent Aujeszky virus.

The percentage survival of the mice after this latter injection is then determined.

The results obtained are presented in the figure, where the survival rate is plotted as ordinate. These results show that a vaccine according to the invention, pGP50–ISA 25, enables twice as large a protection to be conferred as with a vaccine of the prior art comprising only a pGP50 recombinant plasmid in aqueous suspension.

What is claimed is:

1. A composition containing:

(a) a recombinant plasmid comprising a nucleotide sequence encoding a protein, glycoprotein, or peptide; and (b) an emulsion comprising one or two aqueous phases and an oil phase containing a surfactant having a hydrophilic-lipophilic balance (HLB) value of between 1 and 19, said recombinant plasmid being contained in at least one of said phases.

2. The composition according to claim 1, wherein said recombinant plasmid encodes a protein, glycoprotein, or peptide of Aujeszky virus.

3. The composition according to claim 1, wherein said recombinant plasmid encodes the gp50 glycoprotein of Aujeszky virus.

4. The composition according to claim 1, wherein said emulsion is oil-in-water (O/W), water-in-oil (W/O) or water-in-oil-in-water (W/O/W).

5. The composition according to claim 4, wherein said emulsion is O/W.

6. The composition according to claim 1, wherein said surfactant is an ester obtained by condensing a fatty acid with mannitol.

7. The composition according to claim 1, having a viscosity of less than 300 mPa.s at 25° C.

* * * * *